United States Patent [19]

Suzuki et al.

[11] Patent Number: 4,695,581

[45] Date of Patent: Sep. 22, 1987

[54] 2-(3,5-DIALKYL-4-HYDROXYPHENYL)INDOLE DERIVATIVES

[75] Inventors: Yasushi Suzuki, Yokohama; Yukio Hasegawa, Yamato; Michitaka Sato, Kawasaki; Morinobu Saito, Kawasaki; Norio Yamamoto, Kawasaki; Katsuhiko Miyasaka, Atsugi; Takashi Mikami, Yokohama; Katsuhiko Miyazawa, Kawasaki, all of Japan

[73] Assignee: Teikoku Hormone Mfg. Co., Ltd., Minato, Japan

[21] Appl. No.: 770,773

[22] Filed: Aug. 29, 1985

[30] Foreign Application Priority Data

Aug. 31, 1984 [JP] Japan .................. 59-180656

[51] Int. Cl.$^4$ ............... A61K 31/40; C07D 209/12
[52] U.S. Cl. .................................. 514/415; 548/511
[58] Field of Search .................. 548/511; 514/415

[56]    References Cited

U.S. PATENT DOCUMENTS 4,024,155  5/1977  Pigerol et al. .................. 260/319.1
4,543,360  9/1985  von Angerer et al. ............ 514/415

FOREIGN PATENT DOCUMENTS 162573  9/1983  Japan .
130567  7/1985  Japan .

OTHER PUBLICATIONS

Yasuo Isomura et al., Chem. Pharm. Bull., 31(9)3168-3178 (1983).

Primary Examiner—Mary E. Ceperley
Attorney, Agent, or Firm—Wenderoth, Lind & Ponack

[57] ABSTRACT

A compound represented by the formula

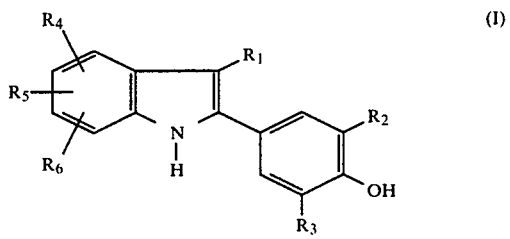

wherein $R_1$ represents a lower alkyl group; each of $R_2$ and $R_3$ represents an alkyl group having 1 to 3 carbon atoms; and each of $R_4$, $R_5$ and $R_6$ represents a hydrogen atom, a halogen atom, a lower alkyl group, a lower alkoxy group, a lower alkanoyloxy group, an aralkyloxy group, a lower alkylthio group, a lower haloalkyl group, a hydroxyl group, a cyano group, a nitro group, an amino group, a mono- or di-(lower alkyl or aralkyl)amino group or a group of the formula

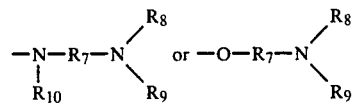

in which $R_7$ represents a lower alkylene group having at least 2 carbon atoms, one of $R_8$ and $R_9$ represents a hydrogen atom or a lower alkyl group and the other represents a lower alkyl group, and $R_{10}$ represents a hydrogen atom or a lower alkyl group; or any two of $R_4$, $R_5$ and $R_6$ which are adjacent to each other, together, represent a lower alkylenedioxy group, and a salt thereof; and a process for production thereof. This compound has 5-lipoxygenase inhibiting activity and is useful as a medicament.

5 Claims, No Drawings

2-(3,5-DIALKYL-4-HYDROXYPHENYL)INDOLE DERIVATIVES

This invention relates to novel 2-(3,5-dialkyl-4-hydroxyphenyl)indole derivatives, and more specifically, to compounds represented by the formula

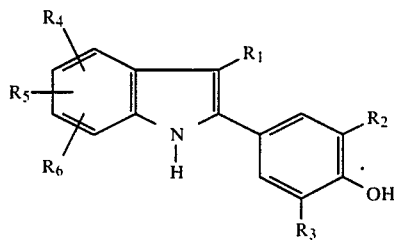

wherein $R_1$ represents a lower alkyl group; each of $R_2$ and $R_3$ represents an alkyl group having 1 to 3 carbon atoms; and each of $R_4$, $R_5$ and $R_6$ represents a hydrogen atom, a halogen atom, a lower alkyl group, a lower alkoxy group, a lower alkanoyloxy group, an aralkyloxy group, a lower alkylthio group, a lower haloalkyl group, a hydroxyl group, a cyano group, a nitro group, an amino group, a mono- or di-(lower alkyl or aralkyl)amino group or a group of the formula

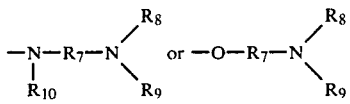

in which $R_7$ represents a lower alkylene group having at least 2 carbon atoms, one of $R_8$ and $R_9$ represents a hydrogen atom or a lower alkyl group and the other represents a lower alkyl group, and $R_{10}$ represents a hydrogen atom or a lower alkyl group; or any two of $R_4$, $R_5$ and $R_6$ which are adjacent to each other, together, represent a lower alkylenedioxy group, and salts of these compounds, a process for production thereof, and the use of thereof as medicines, particularly as a lipoxygenase inhibitor.

With regard to 2-(3,5-dialkyl-4-hydroxyphenyl)indole derivatives, U.S. Pat. No. 4,024,155 discloses that for example, 2-(3,5-dimethyl-4-hydroxyphenyl)indole is useful as a stabilizer for vinyl chloride polymers. Y. Isomura et al. discloses in Chem. Pharm. Bull., 31, 3168–3178 (1983) that a certain 2-(3,5-di-tert-butyl-4-hydroxyphenyl)indole has anti-inflammatory activity.

Previously, the present inventors disclosed certain indole derivatives having 5-lipoxygenase inhibiting activity in which a $C_3$-$C_{12}$ alkyl or alkenyl group is substituted at the 1-position, and a p-substituted phenyl group is bonded to the 2-position (Japanese Laid-Open Patent Publication No. 162573/1983).

The present inventors have now found that the aforesaid 2-(3,5-dialkyl-4-hydroxyphenyl)indole derivatives of formula (I) are novel compounds not described in the prior literature and have an excellent action of inhibiting lipoxygenase for polyunsaturated fatty acids.

A polyunsaturated fatty acid, typically arachidonic acid, is a constituent of a phospholipid present in a biological membrane, and by various stimulations such as an inflammation-inducing stimulation or an antigen-antibody reaction (immunological stimulation), is liberated from the biological membrane into the cells. The liberated arachidonic acid is usually metabolized by cyclooxygenase and lipoxygenase. A slow reacting substance of anaphylaxis (SRS-A) formed by metabolization of arachidonic acid by 5-lipoxygenase is considered to be one of the important substances which participate in an allergic reaction and cause an allergic symptom. Peroxidized fatty acids, products of metabolization of polyunsaturated fatty acids by lipoxygenase, exert biologically deleterious effects; for example, they inhibit the formation of prostacyclin which plays an important role in the defense of a biological tissue.

Heretofore, 3-amino-1-(3-trifluoromethylphenyl)-2-pyrazoline [BW755C] and 5,8,11,14-eicosatetraynoic acid, for example, have been known as lipoxygenase inhibitors. These compounds, however, lack specificity and inhibit not only lipoxygenase but also cyclooxygenase.

In contrast, the compounds of formula (I) provided by this invention specifically inhibit the lipoxygenase, especially 5-lipoxygenase, for polyunsaturated fatty acids, and exhibit an excellent inhibitory action even in oral administration. They are useful for effectively suppressing allergic reactions in asthma, allergic dermatitis, allergic rhinitis, food allergy and other allergic diseases, and for suppressing the production of peroxidized fatty acids, thus defending biological tissues from the deleterious actions of these peroxides.

The term "lower", as used in this specification to qualify a group or a compound, means that the group or compound so qualified has not more than 6, preferably not more than 4, carbon atoms.

In formula (I), examples of the "lower alkyl group" are methyl, ethyl, n-propyl, isopropyl, n-butyl, sec-butyl, tert-butyl, n-pentyl, and n-hexyl groups. Examples of the "lower alkoxy groups" include methoxy, ethoxy, n-propoxy, isopropoxy, n-butoxy, tert-butoxy and n-hexyloxy groups. Examples of the "lower alkanoyloxy group" are acetyloxy and propionyloxy groups. Examples of the "aralkyl group" are benzyl and phenethyl groups. Furthermore, examples of the "lower alkylthio group" include methylthio and ethylthio groups. A trifluoromethyl group is an example of the "lower haloalkyl group".

Examples of the "mono- or di-(lower alkyl or aralkyl)amino group" include diethylamino, methylamino and benzylamino groups. Examples of the group of formula

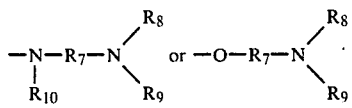

are as follows:

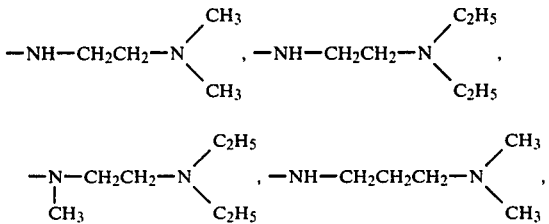

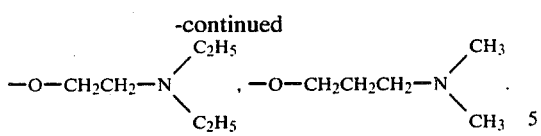

The "halogen atom" includes, for example, fluorine, chlorine and bromine atoms.

Typical examples of the compounds of formula (I) provided by this invention are shown below.

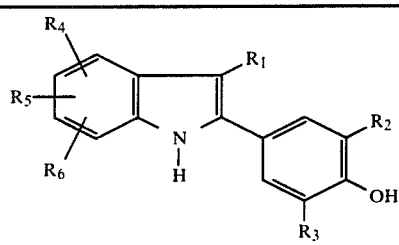

| Comp. No. | $R_1$ | $R_2$ | $R_3$ | $R_4, R_5, R_6$ |
|---|---|---|---|---|
| 1 | $CH_3$ | $CH_3$ | $CH_3$ | H |
| 2 | $C_2H_5$ | $CH_3$ | $CH_3$ | H |
| 3 | $i$-$C_3H_7$ | $CH_3$ | $CH_3$ | H |
| 4 | $CH_3$ | $C_2H_5$ | $C_2H_5$ | H |
| 5 | $C_2H_5$ | $C_2H_5$ | $C_2H_5$ | H |
| 6 | $n$-$C_4H_9$ | $C_2H_5$ | $C_2H_5$ | H |
| 7 | $CH_3$ | $n$-$C_3H_7$ | $n$-$C_3H_7$ | H |
| 8 | $i$-$C_4H_9$ | $n$-$C_3H_7$ | $n$-$C_3H_7$ | H |
| 9 | $CH_3$ | $CH_3$ | $C_2H_5$ | H |
| 10 | $C_2H_5$ | $CH_3$ | $C_2H_5$ | H |
| 11 | $CH_3$ | $CH_3$ | $CH_3$ | 4-Cl |
| 12 | $CH_3$ | $CH_3$ | $CH_3$ | 4-F |
| 13 | $CH_3$ | $CH_3$ | $CH_3$ | 5-Cl |
| 14 | $C_2H_5$ | $CH_3$ | $CH_3$ | 5-Cl |
| 15 | $CH_3$ | $C_2H_5$ | $C_2H_5$ | 5-Br |
| 16 | $CH_3$ | $CH_3$ | $CH_3$ | 6-F |
| 17 | $CH_3$ | $CH_3$ | $CH_3$ | 6-Cl |
| 18 | $C_2H_5$ | $CH_3$ | $CH_3$ | 7-Cl |
| 19 | $CH_3$ | $CH_3$ | $CH_3$ | 7-Br |
| 20 | $CH_3$ | $CH_3$ | $CH_3$ | 5-$CH_3$ |
| 21 | $CH_3$ | $CH_3$ | $CH_3$ | 5-$C_2H_5$ |
| 22 | $C_2H_5$ | $CH_3$ | $CH_3$ | 7-$CH_3$ |
| 23 | $CH_3$ | $CH_3$ | $CH_3$ | 5-$OCH_3$ |
| 24 | $C_2H_5$ | $CH_3$ | $CH_3$ | 5-$OCH_3$ |
| 25 | $CH_3$ | $C_2H_5$ | $C_2H_5$ | 5-$OCH_3$ |
| 26 | $n$-$C_4H_9$ | $CH_3$ | $CH_3$ | 5-$OCH_3$ |
| 27 | $CH_3$ | $CH_3$ | $CH_3$ | 7-$OCH_3$ |
| 28 | $C_2H_5$ | $CH_3$ | $CH_3$ | 7-$OCH_3$ |
| 29 | $CH_3$ | $CH_3$ | $CH_3$ | 5-$OC_2H_5$ |
| 30 | $CH_3$ | $CH_3$ | $CH_3$ | 5-O-$i$-$C_3H_7$ |
| 31 | $CH_3$ | $CH_3$ | $CH_3$ | 7-O-$i$-$C_3H_7$ |
| 32 | $CH_3$ | $CH_3$ | $CH_3$ | 5-$OCOCH_3$ |
| 33 | $C_2H_5$ | $CH_3$ | $CH_3$ | 5-$OCH_2C_6H_5$ |
| 34 | $CH_3$ | $CH_3$ | $CH_3$ | 5-$SCH_3$ |
| 35 | $CH_3$ | $CH_3$ | $CH_3$ | 6-$CF_3$ |
| 36 | $CH_3$ | $CH_3$ | $CH_3$ | 7-OH |
| 37 | $CH_3$ | $CH_3$ | $CH_3$ | 5-CN |
| 38 | $CH_3$ | $CH_3$ | $CH_3$ | 5-$NO_2$ |
| 39 | $CH_3$ | $CH_3$ | $CH_3$ | 5-$NH_2$ |
| 40 | $C_2H_5$ | $CH_3$ | $CH_3$ | 5-$NH_2$ |
| 41 | $CH_3$ | $C_2H_5$ | $C_2H_5$ | 7-$NH_2$ |
| 42 | $CH_3$ | $CH_3$ | $CH_3$ | 5-$NHCH_3$ |
| 43 | $CH_3$ | $CH_3$ | $CH_3$ | 5-$N(CH_3)_2$ |
| 44 | $CH_3$ | $CH_3$ | $CH_3$ | 5-$NHCH_2C_6H_5$ |
| 45 | $CH_3$ | $CH_3$ | $CH_3$ | 5-$NHCH_2CH_2N(C_2H_5)_2$ |
| 46 | $CH_3$ | $CH_3$ | $CH_3$ | 5-$NHCH_2CH_2CH_2N(CH_3)_2$ |
| 47 | $CH_3$ | $CH_3$ | $CH_3$ | 5-$OCH_2CH_2N(C_2H_5)_2$ |
| 48 | $CH_3$ | $CH_3$ | $CH_3$ | 5-Cl, 6-Cl |
| 49 | $C_2H_5$ | $CH_3$ | $CH_3$ | 5-Cl, 7-Cl |
| 50 | $CH_3$ | $CH_3$ | $CH_3$ | 5-$OCH_3$, 6-$OCH_3$ |
| 51 | $C_2H_5$ | $CH_3$ | $CH_3$ | 5-$OCH_3$, 6-$OCH_3$ |
| 52 | $CH_3$ | $C_2H_5$ | $C_2H_5$ | 5-$OCH_3$, 6-$OCH_3$ |
| 53 | $CH_3$ | $CH_3$ | $CH_3$ | 5-$OCH_3$, 6-$OCH_3$, 7-$OCH_3$ |
| 54 | $CH_3$ | $CH_3$ | $CH_3$ | 5-O—$CH_2$—O—6 |
| 55 | $C_2H_5$ | $CH_3$ | $CH_3$ | 5-O—$CH_2$—O—6 |

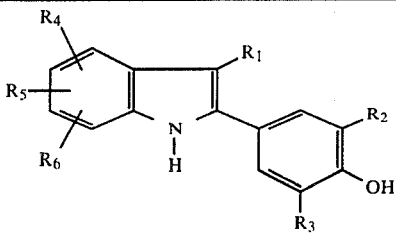

| Comp. No. | $R_1$ | $R_2$ | $R_3$ | $R_4, R_5, R_6$ |
|---|---|---|---|---|
| 56 | $CH_3$ | $CH_3$ | $CH_3$ | 4-O—$CH_2CH_2$—O—5 |
| 57 | $CH_3$ | $CH_3$ | $CH_3$ | 5-O—$CH_2CH_2$—O—6 |

In the compounds of formula (I), $R_1$ is preferably a methyl or ethyl group, and $R_2$ and $R_3$ are preferably a methyl or ethyl group, especially a methyl group.

Preferred species of the compounds of formula (I) are those of the following formula

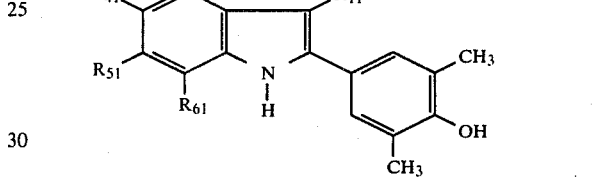

wherein $R_{11}$ represents a methyl or ethyl group, one or two of $R_{41}$, $R_{51}$ and $R_{61}$ represent a hydrogen atom, a lower alkyl group, a lower alkoxy group, a lower alkanoyloxy group, a benzyloxy group, a lower alkylthio group, an amino group, or a group of the formula

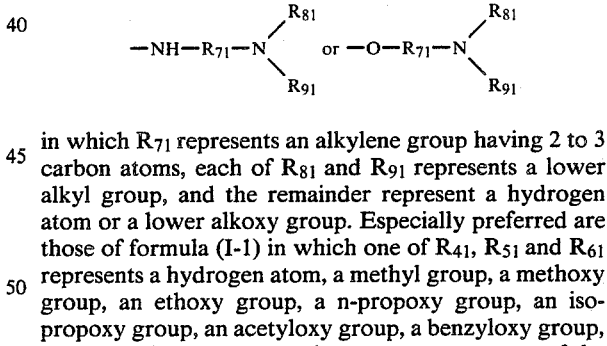

in which $R_{71}$ represents an alkylene group having 2 to 3 carbon atoms, each of $R_{81}$ and $R_{91}$ represents a lower alkyl group, and the remainder represent a hydrogen atom or a lower alkoxy group. Especially preferred are those of formula (I-1) in which one of $R_{41}$, $R_{51}$ and $R_{61}$ represents a hydrogen atom, a methyl group, a methoxy group, an ethoxy group, a n-propoxy group, an isopropoxy group, an acetyloxy group, a benzyloxy group, a methylthio group, an amino group, or a group of the formula

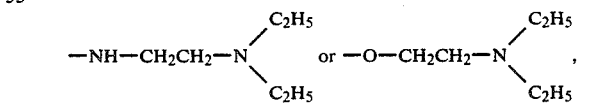

and the remainder represent a hydrogen atom or a methoxy group, and above all $R_{61}$ is preferably a hydrogen atom.

From the standpoint of pharmacological effects of the compounds of formula (I-1), it is advantageous that $R_{41}$ represents a hydrogen atom, a lower alkyl group, a lower alkoxy group, or an amino group, and $R_{51}$ and $R_{61}$ represent a hydrogen atom or a lower alkoxy group.

Among these, the following compounds are particularly preferred.

2-(4-Hydroxy-3,5-dimethylphenyl)-5-methoxy-3-methylindole,
2-(4-hydroxy-3,5-dimethylphenyl)-3-methylindole,
2-(4-hydroxy-3,5-dimethylphenyl)-3,5-dimethylindole,
5-amino-2-(4-hydroxy-3,5-dimethylphenyl)-3-methylindole,
2-(4-hydroxy-3,5-dimethylphenyl)-3-methyl-5-isopropoxyindole,
2-(4-hydroxy-3,5-dimethylphenyl)-5,6-dimethoxy-3-methylindole, and
3-ethyl-2-(4-hydroxy-3,5-dimethylphenyl)-5-methoxyindole.

The compounds of formula (I) can exist as salts. Examples of such salts are salts with meals such as sodium or potassium, salts with inorganic acids such as hydrochloric acid, sulfuric acid or phosphoric acid, or salts with organic acids such as acetic acid or citric acid. Those which are pharmaceutically acceptable are preferred.

The compounds of formula (I) can be produced in accordance with the Fischer indole synthetic method known per se.

For example, they can be produced by reacting a phenylhydrazine compound of the formula

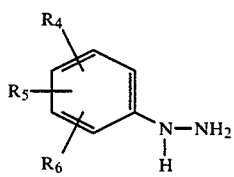
(II)

wherein $R_4$, $R_5$ and $R_6$ are as defined hereinabove, or its salt with a compound of the formula

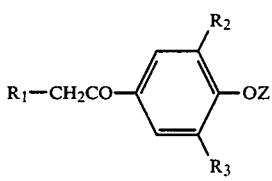
(III)

wherein Z represents a hydrogen atom, a lower alkyl group or an aralkyl group, and $R_1$, $R_2$ and $R_3$ are as defined above, cyclizing the resulting compound of the formula

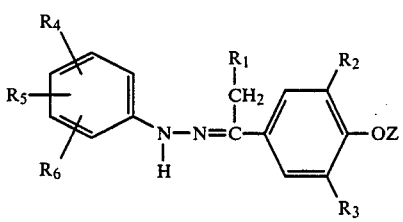
(IV)

wherein $R_1$, $R_2$, $R_3$, $R_4$, $R_5$, $R_6$ and Z are as defined above, to produce a compound of the formula

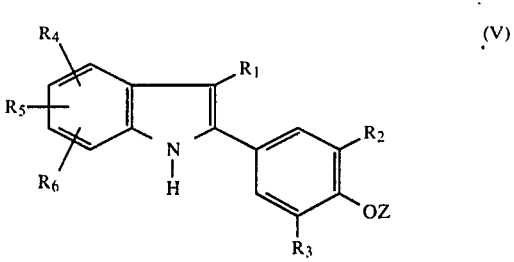
(V)

wherein $R_1$, $R_2$, $R_3$, $R_4$, $R_5$, $R_6$ and Z are as defined above, and thereafter when Z is a lower alkyl group or an aralkyl group, splitting off the group Z from the compound of formula (V).

In the above reaction, the reaction of the compound of formula (II) or its salt with the compound of formula (III) is carried out usually in a suitable solvent, for example an alcohol such as methanol, ethanol or propanol, an ether such as tetrahydrofuran or dioxane, or a mixture of at least two of these. The reaction temperature is not critical, and may be varied widely depending upon the types of the starting materials, the type of the solvent, etc. Generally, the reaction is desirably carried out at room temperature to the refluxing temperature of the reaction mixture, preferably 50° C. to the refluxing temperature of the reaction mixture. Under these temperature conditions, the reaction can usually be terminated in several minutes to 5 hours.

The above reaction may be carried out in the presence of a suitable acid catalyst. Examples of the acid catalyst that can be used include organic acids such as trifluoroacetic acid and glacial acetic acid, and inorganic acids such as hydrochloric acid and sulfuric acid. The catalyst can be used generally in an amount of 1/1000 to 10 moles, preferably 1/10 to 1 mole, per mole of the compound of formula (II). The acid catalyst is not particularly required when the compound of formula (II) is used in the form of a hydrochloride or sulfate.

The amount of the compound of formula (III) relative to the compound of formula (II) or its salt is neither restricted in particular. Advantageously, however, the compound of formula (III) is used usually in a proportion of 1 to 2 moles, especially 1 to 1.1 moles, per mole of the compound of formula (II) or its salt.

Most of the compounds of formula (II) used as the starting material in the above reaction are known. Furthermore, at least some of the compounds of formula (III) to be reacted with the compounds of formula (II) are known [see Bull. Soc. Chim. France, (1966), 640].

Any novel compounds of formula (III) can be produced by known methods, for example by the Fries rearrangement or the Friedel-Crafts reaction.

The above reaction gives the compound of formula (IV9 which can be subjected to the cyclization reaction either as such or after it is separated from the reaction mixture by a common procedure.

Cyclization of the compound of formula (IV) may be carried out by treating the compound of formula (IV) with polyphosphoric acid (including a mixture of phosphorus pentoxide and phosphoric acid in arbitrary ratios) or an organic ester thereof (for example, lower alkyl esters of polyphosphoric acid such as ethyl polyphosphate, and trialkyl silyl esters of polyphosphoric acid such as trimethylsilyl polyphosphate), or a Lewis acid such as tin tetrachloride or titanium tetrachloride in the absence of solvent or in a suitable solvent, for example a halogenated hydrocarbon such as methylene chloride, chloroform, carbon tetrachloride or tetrachloroethane; or treating the compound of formula (IV) with an acidic alcohol solvent. The first-mentioned treatment with polyphosphoric acid or its organic acid ester or a Lewis acid may generally be carried out at 40° to 150° C., preferably 60° to 120° C. The latter treatment with the acidic alcohol solvent (for example, an alcohol such as methanol, ethanol, propanol, isopropanol or ethylene glycol saturated with anhydrous hydrogen chloride) may be carried out generally at room temperature to the refluxing temperature of the reaction mixture, preferably 50° C. to the refluxing temperature of the reacton mixture.

The amount of the polyphosphoric acid or its organic acid ester or the Lewis acid is not critical. Advantageously, it is at least equal in weight to the compound of formula (IV), preferably in an amount 5 to 50 times the weight of the compound of formula (IV). The acidic alcohol solvent may be used in an amount of at least about 1 equivalent per mole of the compound of formula (IV) as the equivalent of the acid in the acidic alcoholic solvent, preferably in a large excess.

The above cyclization reaction gives the compound of formula (V) in good yields.

When Z in the resulting compound of formula (V) represents a lower alkyl group, the compound may be converted into the compound of formula (I) by dealkylating it and thereby splitting off the group Z. The dealkylation reaction may be carried out by methods known per se. For example, it can be carried out by treating the compound of formula (V) in the absence of solvent, or in a suitable solvent such as tetralin or quinoline together with a pyridinium halide (such as pyridinium chloride) or a hydrohalic acid (such as hydrochloric acid or hydrobromic acid) under heat, for example at a temperature of 150° to 200° C.

When Z is an aralkyl group, the aralkyl group can be split off from the compound of formula (V) by a method known per se, for example by hydrogenating the compound of formula (V) in an inert organic solvent such as ethanol or propanol in the presence of a palladium catalyst or a nickel catalyst under a pressure ranging from atmospheric pressure to several atmospheres.

The compound of formula (I) so obtained can be separated from the reaction mixture and/or purified by methods known per se, such as extraction, filtration, distillation, recrystallization, column chromatography, or thin-layer chromatography.

Some of the compounds of formula (I) can be produced also by the known Bischler-Moehlan indole synthesis method. Specifically, this method is carried out, for example, by reacting an aniline compound represented by the formula

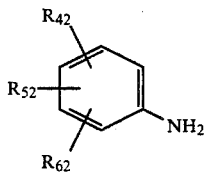
(VI)

wherein each of $R_{42}$, $R_{52}$ and $R_{62}$ represents a hydrogen atom, a halogen atom, a lower alkyl group, a lower alkoxy group, a lower alkanoyloxy group, an aralkyloxy group, a lower alkylthio group, a lower haloalkyl group, a cyano group, a nitro group, or a group of the formula

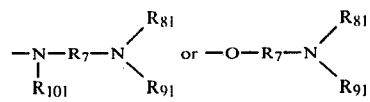

in which $R_7$ represents a lower alkylene group having at least 2 carbon atoms, each of $R_{81}$ and $R_{91}$ represents a lower alkyl group, and $R_{101}$ represents a lower alkyl group, or any two of $R_{42}$, $R_{52}$ and $R_{62}$ which are adjacent to each other, together, represent a lower alkylenedioxy group, or its salt with a compound represented by the formula

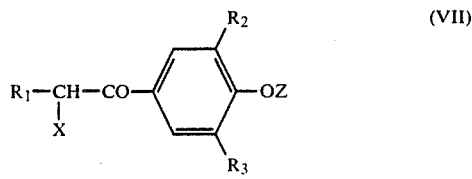
(VII)

wherein X represents a halogen atom, preferably a chlorine or bromine atom, and $R_1$, $R_2$, $R_3$ and Z are as defined above, to form a compound represented by the formula

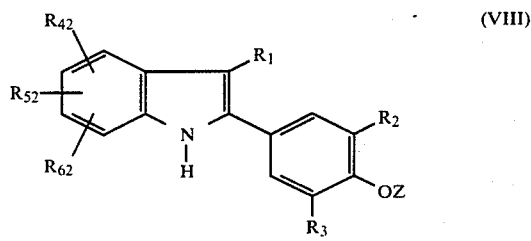
(VIII)

wherein $R_1$, $R_2$, $R_3$, $R_{42}$, $R_{52}$, $R_{62}$ and Z are as defined above, and thereafter treating the compound of formula (VIII) in the same manner as above to form the desired compound of the formula

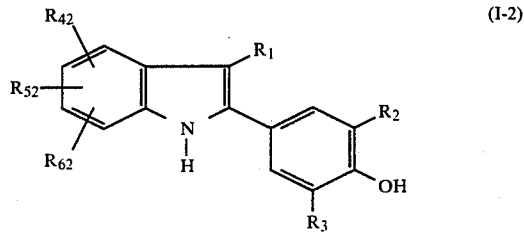
(I-2)

wherein $R_1$, $R_2$, $R_3$, $R_{42}$, $R_{52}$ and $R_{62}$ are as defined above.

The reaction of the compound of formula (VI) or its salt with the compound of formula (VII) can be carried out in the absence of solvent or a suitable inert organic solvent, for example a hydrocarbon such as toluene, xylene, tetralin or decalin, at a temperature of generally 100° to 200° C., preferably 130° to 170° C. The above reaction may be carried out in the presence of an acid binder, for example an organic base such as dimethylaniline, diethylaniline or pyridine, or an excessive amount of the aniline compound of formula (VI) or its salt. The amount of the acid binder may generally be about 1 to 5 moles per mole of the compound of formula (VII). Preferably, this reaction is carried out in an inert gas while shutting off light.

The amount of the compound of formula (VI) or its salt relative to the compound of formula (VII) is neither limited. Advantageously, the compound of formula (VI) or its salt is used in an amount of at least 1 mole, preferably 2 to 10 moles, per mole of the compound of formula (VII) to make the compound of formula (VI) serve also as the acid binder.

Most of the compounds of formula (VI) or their salts used as the starting material in the above reaction are known, and most of the compounds of formula (VII) to be reacted with the above compounds are also known. Any novel compounds of formula (VII) may be produced, for example, by reacting the compound of formula (III) with bromine in an inert organic solvent such as carbon tetrachloride, chloroform or dichloromethane at the refluxing temperature of the reaction mixture under irradiation of light, or by reacting the compound of formula (III) with chlorine in the presence of red phosphorus.

When at least one of $R_4$, $R_5$ and $R_6$ in the resulting compound of formula (I) is a hydrogen atom, the hydrogen atom may be replaced by a nitro group by, for example, reacting the compound (I) with potassium nitrate in concentrated sulfuric acid in accordance with an ordinary method of nitrating the aromatic ring [see, for example, J. Org. Chem., 31, 65–69 (1966)]. When $R_4$, $R_5$ or $R_6$ is a nitro group, it can be converted into an amino group by catalytically reducing it in a customary manner [see, for example, Org. Synth. Coll. I., 240–241 (1948)]. When $R_4$, $R_5$ or $R_6$ is a bromine atom, it can be converted into a cyano group by treating the compound (I) with copper (I) cyanide by using a known reaction [see, for example, Tetrahedron, 23, 3823–3827 (1967)].

The compound of formula (I) in which at least one of $R_4$, $R_5$ and $R_6$ represents a lower alkoxy group may be converted by the same dealkylation reaction as described above ilnto a compound (I) in which the lower alkoxy group is replaced by a hydroxyl group. The hydroxyl group on the indole ring in formula (I) may be converted into a lower alkanoyloxy group by reacting it with, for example, a lower alkanoyl halide or a lower alkanoic acid anhydride by an ordinary acylation method. When it is reacted with a compound of the formula

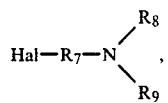

the hydroxyl group on the indole ring can be converted into a group of the formula

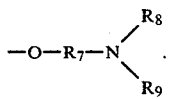

The amino group on the indole ring of formula (I) may be converted into a mono- or di-(lower alkyl or aralkyl)amino group or a group of the formula

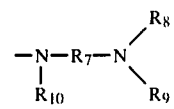

by an ordinary method of alkylating the amino group [see, for example, Ann., 598, 174–185 (1956)].

More specific reaction conditions for the aforesaid modifications of the substituents on the indole ring of the compound of formula (I) are described in Examples 31 to 38 given hereinbelow.

As required, the compound of formula (I) produced by the process described above can be converted into its salt. This can be carried out in a manner known per se by treating it with an acid or an inorganic base in the absence of solvent or in a suitable inert solvent in accordance with a conventional method.

The compounds of formula (I) provided by the present invention have the activity of inhibiting the formation of lipoxygenase metabolites by selectively inhibiting the lipoxygenase, particularly 5-lipoxygenase, for polyunsaturated fatty acids present in biological membranes. Accordingly, the compounds of formula (I) provided by this invention are useful for inhibiting physiological and pathological activities which are induced by the lipoxygenase metabolites and are biologically undesirable.

The compounds of formula (I) are characterized by exhibiting the aforesaid activity strongly even in oral administration, and are therefore extremely useful.

More specifically, the compounds of formula (I) provided by this invention can be used as an anti-asthma agent, an antiallergic agent (for the prevention and treatment of allergic dermatitis, allergic rhinitis, urticaria, gastrointestinal tract allergy, food allergy and other allergic diseases), an anti-rheumatic agent, an antithrombotic agent, an agent for treating arteriosclerosis, an agent for treating vasospasm following subarachnoid homorrhage, an agent for treating impaired cerebral circulation, an agent for treating coronary insufficiency, an agent for treating ischemic myocardial infarction, an agent for treating ischemic cerebral embolism, an agent for regulating immunity, an agent for treating ulcerative colitis, and an agent for treating psoriasis.

The following animal experiments demonstrate that the compounds of formula (I) have the activity of inhibiting lipoxygenase for polyunsaturated fatty acids.

(1) Preparation of $A_{23187}$-induced pleurisy

Under ether anaesthesia, 0.2 ml of 100 μM $A_{23187}$ (prepared by adding injectable distilled water in a 2 mM $A_{23187}$ ethanol solution) was administered intrapleurally to rats (Wistar-strain, male, 11 weeks old). Twenty minutes after the administration, the rats were exsanguinated and the pleural exudate was harvested. The test compound was suspended or dissolved in a 0.5% carboxymethyl cellulose solution containing 2% Tween, and orally administered to the animals 60 minutes before the intrapleural administration of $A_{23187}$.

(2) Measurement of SRS-A-like active substance

To the exudate obtained in (1) was added 4 times its volume of ice-cooled ethanol. They were well mixed, and then centrifuged. The supernatant was concentrated under reduced pressure, and 1.0 ml of 0.01M acetate buffer (pH 5.9) was added to the residue. The solution was added to SEP-PAK ® ($C_{18}$) and SRS-A- like active substance was partially purified. Fractions eluted with 5 ml of 60% ethanol/0.01M acetate buffer (pH 5.9) were collected, and the solvent was evaporated under reduced pressure. The residue was dissolved in purified water in an amount corresponding to the amount of the exudate.

The SRS-A-like active substance was assayed on the basis of contraction of the ileum of guinea pig (Hartley-strain, male, body weight 400–500 g) in the presence of atropine and Pyrilamine. The presence of SRS-A was confirmed by the fact that the contraction of the isolated ileum by the test solution was antagonized by FPL-55712 which is a specific antagonist for SRS-A.

The results are shown in the following table. The activity of inhibiting the formation of an SRS-A-like active substance is indicated as the percent inhibition based on a control group to which only the solvent was administered.

| Test compound (Example No.) | Dose (mg/kg, p.o.) | Inhibitory activity on the formation of SRS-A-like active substance (%) |
|---|---|---|
| 1 | 10 | 66.2 |
| 5 | 10 | 54.7 |
| 8 | 10 | 28.7 |
| 9 | 10 | 58.4 |
| 10 | 10 | 41.0 |
| 14 | 10 | 30.7 |
| 16 | 10 | 37.5 |
| 24 | 10 | 70.4 |
| 30 | 10 | 58.0 |
| | 30 | 90.2 |
| 33 | 10 | 68.1 |
| 35 | 10 | 39.1 |
| 36 | 10 | 35.4 |
| 37 | 10 | 43.7 |
| 38 | 10 | 38.3 |
| 43 | 10 | 46.2 |
| 44 | 10 | 46.9 |
| | 30 | 87.2 |
| 45 | 10 | 52.7 |
| 46 | 10 | 22.9 |
| | 30 | 74.2 |
| 48 | 10 | 28.3 |
| 50 | 10 | 21.5 |

Toxicity

The test compound was suspended in a 10% gum arabic solution, and orally administered to SD-strain male rats (body weight 100–115 g) in 5-membered groups. The animals were observed for 2 weeks. No case of death was observed when the compound of Example 1 was administered in a dose of 5 g/kg.

The compound of formula (I) provided by this invention can be administered orally, parenterally (for example, intramuscularly, intravenously, subcutaneously, or intrarectally), or topically to man and other mammals for the treatment or prevention of various diseases induced by the participation of lipoxygenase metabolites.

For use as medicaments, the compound of formula (I) may be formulated into various forms suitable for oral, parenteral or topical administration. For example, the compound of this invention can be formulated by using various nontoxic carriers or diluents normally used in drugs of this type, for example, vehicles, binders, lubricants, disintegrants, antiseptics, isotonizing agents, stabilizers, dispersants, antioxidants, coloring agents, flavoring agents, buffers, propellants and surface-active agents.

Depending upon their uses, such medicaments may be formulated into tablets, capsules, granules, powders, pellets, pills, trouches, suppositories, ointments, patches, injectable preparations, syrups, and aerosols. Specific examples of the nontoxic carriers or diluents which can be used include starch, gelatin, glucose, lactose, fructose, maltose, magnesium carbonate, talc, magnesium stearate, methyl cellulose, carboxymethyl cellulose or its salts, gum arabic, polyethylene glycol, alkyl p-hydroxybenzoates, syrup, ethanol, propylene glycol, Vaseline, carbowax, glycerol, sodium chloride, sodium sulfite, sodium phosphate, citric acid, dichlorodifluoromethane, 1,2-dichlorotetrafluoroethane and sorbitan trioleate.

The medicaments may also contain other therapeutically effective drugs.

The dose of the compound of formula (I) can be varied widely depending upon the type of the animal to be treated, the route of administration, the severity of the condition, the diagnosis of a physician, etc. Generally, it may be 0.1 to 50 mg/kg, preferably 0.2 to 20 mg/kg, per day. It is of course possible to administer the compound of formula (I) in a dose larger than the above-specified upper limit or smaller than the above-specified lower limit according to the severity of the patient's condition and the physician's diagnosis. The above dose may be taken once a day or in several portions a day.

The following examples further illustrate the present invention.

EXAMPLE 1

5.1 g of 2,6-dimethyl-4-propionylphenol and 5.0 g of 4-methoxyphenylhydrazine hydrochloride were dispersed in 30 ml of isopropanol, and the dispersion was refluxed for 20 hours in a nitrogen stream. Water was added to the reaction mixture, and the precipitated crystals were collected by filtration. The crystals were dissolved in ethyl acetate, and washed with a 5% aqueous sodium hydroxide solution, water, 2N hydrochloric acid and water. The organic layer was dried, and the solvent was evaporated. Recrystallization of the resulting crude crystals from ethanol-hexane gave 5.8 g of 2-(4-hydroxy-3,5-dimethylphenyl)-5-methoxy-3-methylindole.

Melting point: 158.2°–158.8° C.

IR, $\nu_{max}^{KBr}$ ($cm^{-1}$): 3440, 3300, 2905, 1480, 1290, 1210.

NMR, $\delta_{CDCl_3}^{ppm}$: 2.25 (6H, s), 2.32 (3H, s), 3.3 (1H), 3.75 (3H, s), 6.62 (1H, q, J=8 Hz, 3 Hz), 6.9 (1H, d, J=3 Hz), 7.15 (1H, d, J=8 Hz), 7.17 (2H, s), 8.3 (1H).

In the same way as in Example 1, Examples 2 to 28 were carried out to synthesize the compounds indicated.

EXAMPLE 2

4-Chloro-2-(4-hydroxy-3,51-dimethylphenyl)-3-methylindole

Melting point: 167.2°–168.2° C.

NMR, $\delta_{CDCl_3}^{ppm}$: 2.3 (6H, s), 2.60 (3H, s), 4.68 (1H), 7.1 (2H, s), 6.9–7.3 (3H, m), 7.9 (1H).

EXAMPLE 3

4-Bromo-2-(4-hydroxy-3,5-dimethylphenyl)-3-methylindole

Melting point: 170.7°–171.7° C.

NMR, $\delta_{CDCl_3}^{ppm}$: 2.30 (6H, s), 2.61 (3H, s), 4.70 (1H, s), 6.75–7.31 (5H, m), 7.90 (1H).

EXAMPLE 4

5-Chloro-2-(4-hydroxy-3,5-dimethylphenyl)-3-methylindole

Melting point: 125.9°–126.3° C.
NMR, $\delta_{CDCl_3}^{ppm}$: 2.3 (6H, s), 2.35 (3H, s), 4.7 (1H, s), 7.12 (2H, s), 7.3 (3H, m), 7.85 (1H).

EXAMPLE 5

2-(4-Hydroxy-3,5-dimethylphenyl)-3,5-dimethylindole

Melting point: 143.2°–143.7° C.
IR, $\nu_{max}^{KBr}$ (cm$^{-1}$): 3440, 3350, 2900, 1450, 1330, 1205. 1190, 790.
NMR, $\delta_{CDCl_3}^{ppm}$: 2.29 (6H, s), 2.37 (3H, s), 2.45 (3H, s), 4.64 (1H, s), 7.12 (2H, s), 7.15 (3H, m), 7.72 (1H).

EXAMPLE 6

5-Fluoro-2-(4-hydroxy-3,5-dimethylphenyl)-3-methylindole

Melting point: 102.0°–103.8° C.
NMR, $\delta CDCl_3^{ppm}$: 2.29 (6H, s), 2.34 (3H, s), 4.71 (1H), 7.05 (3H, m), 7.12 (2H, s), 7.80 (1H).

EXAMPLE 7

5-Bromo-2-(4-hydroxy-3,5-dimethylphenyl)-3-methylindole

Melting point: 126.0°–126.3° C.
NMR, $\delta_{CDCl_3}^{ppm}$: 2.25 (6H, s), 2.32 (3H, s), 3.26 (1H, s), 7.18 (2H, s), 7.15 (1H, d—d, J=10 Hz, 2.0 Hz), 7.24 (1H, d, J=10 Hz), 7.55 (1H, d, J=2.0 Hz), 8.34 (1H, s).

EXAMPLE 8

5-Ethoxy-2-(4-hydroxy-3,5-dimethylphenyl)-3-methylindole

Melting point: 135.4°–136.0° C.
NMR, $\delta_{(CD_3)_2SO}^{ppm}$: 1.33 (3H, t, d=7 Hz), 2.26 (6H, s), 2.33 (3H, s), 3.32 (1H), 4.00 (2H, q, J=7 Hz), 6.64 (1H, q, J=9 Hz, 3 Hz), 6.90 (1H, d, J=3 Hz), 7.16 (1H, d, J=9 Hz), 7.19 (2H, s), 8.29 (1H).

EXAMPLE 9

2-(4-Hydroxy-3,5-dimethylphenyl)-3-methyl-5-isopropoxyindole

Melting point: 125.1°–125.8° C.
IR, $\nu_{max}^{KBr}$ (cm$^{-1}$): 3448, 1480, 1208.
NMR, $\delta_{CDCl_3}^{ppm}$: 1.35 (6H, d, J=6 Hz), 2.26 (6H, s), 2.33 (3H, s), 4.50 (1H, septet, J=6 Hz), 4.73 (1H), 6.75 (1H, q, J=9 Hz), 7.01 (1H, d, J=3 Hz), 7.12 (1H, d, J=9 Hz), 7.09 (2H, s), 7.71 (1H).

EXAMPLE 10

2-(4-hydroxy-3,5-dimethylphenyl)-3-methyl-5-methylthioindole

Melting point: 159.6°–160.7° C.
NMR, $\delta_{CDCl_3}^{ppm}$: 2.29 (6H, s), 2.37 (3H, s), 2.50 (3H, s), 4.69 (1H), 7.1–7.2 (4H, m), 7.52 (1H, m), 7.85 (1H).

EXAMPLE 11

6-Fluoro-2-(4-hydroxy-3,5-dimethylphenyl)-3-methylindole

Melting point: 136.6°–137.7° C.
NMR, $\delta_{CDCl_3}^{ppm}$: 2.27 (6H, s), 2.36 (3H, s), 4.68 (1H), 7.12 (2H, s), 6.6–7.55 (3H, m), 7.75 (1H).

EXAMPLE 12

6-Chloro-2-(4-hydroxy-3,5-dimethylphenyl)-3-methylindole

Melting point: 171.0°–171.1° C.
NMR, $\delta_{CDCl_3}^{ppm}$: 2.30 (6H, s), 2.37 (3H, s), 4.69 (1H), 7.12 (2H, s), 6.95–7.50 (3H, m), 7.85 (1H).

EXAMPLE 13

6-Bromo-2-(4-hydroxy-3,5-dimethylphenyl)-3-methylindole

Melting point: 158.1°–158.7° C.
NMR, $\delta_{CDCl_3}^{ppm}$: 2.30 (6H, s), 2.37 (3H, s), 4.70 (1H, s), 7.08–7.45 (5H, m), 7.82 (1H).

EXAMPLE 14

2-(4-Hydroxy-3,5-dimethylphenyl)-3,6-dimethylindole

Melting point: 123.0°–124.1° C.
NMR, $\delta_{CDCl_3}^{ppm}$: 2.27 (6H, s), 2.38 (3H, s), 2.43 (3H, s), 4.61 (1H), 6.91 (1H, d—d, J=8.1 Hz, 1.8 Hz), 7.00 (1H, d, J=1.8 Hz), 7.10 (2H, s), 7.40 (1H, d—d, J=8.1 Hz, 1.8 Hz), 7.65 (1H).

EXAMPLE 15

2-(4-Hydroxy-3,5-dimethylphenyl)-3-methyl-6-trifluoromethylindole

Melting point: 90.0°–90.6° C.
NMR, $\delta_{CDCl_3}^{ppm}$: 2.31 (6H, s), 2.40 (3H, s), 4.72 (1H, s), b 7.15 (2H, s), 7.14–7.67 (3H, m), 8.02 (1H).

EXAMPLE 16

2-(4-Hydroxy-3,5-dimethylphenyl)-3,7-dimethylindole

Melting point: 128.3°–130.0° C.
NMR, $\delta_{CDCl_3}^{ppm}$: 2.30 (6H, s), 2.39 (3H, s), 2.48 (3H, s), 4.65 (1H), 7.05 (3H, m), 7.18 (2H, s), 7.75 (1H).

EXAMPLE 17

7-Fluoro-2-(4-hydroxy-3,5-dimethylphenyl)-3-methylindole

Melting point: 98.2°–99.8° C.
NMR, $\delta_{CDCl_3}^{ppm}$: 2.30 (6H, s), 2.40 (3H, s), 4.70 (1H), 6.75–7.4 (3H, m), 7.17 (2H, s), 8.0 (1H).

EXAMPLE 18

7-Chloro-2-(4-hydroxy-3,5-dimethylphenyl)-3-methylindole

Melting point: 118.0°–118.8° C.
NMR, $\delta_{CDCl_3}^{ppm}$: 2.30 (6H, s), 2.39 (3H, s), 4.70 (1H), 7.0 (1H, t, J=6 Hz), 7.13 (1H, q, J=6 Hz, 3 Hz), 7.42 (1H, q, J=6 Hz, 3 Hz), 8.05 (1H).

EXAMPLE 19

7-Bromo-2-(4-hydroxy-3,5-dimethylphenyl)-3-methylindole

Melting point: 125.3°–126.2° C.
NMR, $\delta_{CDCl_3}^{ppm}$: 2.28 (6H, s), 2.37 (3H, s), 4.68 (1H), 6.93 (1H, d—d J=8.0 Hz), 7.27 (1H, d—d, J=8.0 Hz, 2.0 Hz), 7.45 (1H, d—d, J=8.0 Hz, 2.0 Hz), 8.00 (1H).

EXAMPLE 20

2-(4-Hydroxy-3,5-dimethylphenyl)-7-methoxy-3-methylindole

Melting point: 100.9°–101.2° C.
NMR, $\delta_{CDCl_3}^{ppm}$: 2.28 (6H, s), 2.40 (3H, s), 3.94 (3H, s), 4.69 (1H, s), 6.54–7.26 (5H, m), 8.16 (1H).

EXAMPLE 21

4,5-Dichloro-2-(4-hydroxy-3,5-dimethylphenyl)-3-methylindole

Melting point: 185.8°–186.3° C.
NMR, $\delta_{CDCl_3}^{ppm}$: 2.31 (6H, s), 2.60 (3H, s), 7.12 (2H, s), 7.16 (2H, d, J=10.0 Hz), 7.95 (1H).

EXAMPLE 22

5,6-Dichloro-2-(4-hydroxy-3,5-dimethylphenyl)-3-methylindole

Melting point: 171.9°–172.5° C.
NMR, $\delta_{CDCl_3}^{ppm}$: 2.30 (6H, s), 2.32 (3H, s), 4.72 (1H, s), 7.12 (2H, s), 7.33 (1H, s), 7.55 (1H, s), 7.85 (1H).

EXAMPLE 23

5,7-Dichloro-2-(4-hydroxy-3,5-dimethylphenyl)-3-methylindole

Melting point: 177.4°–179.2° C.
NMR, $\delta_{CDCl_3}^{ppm}$: 2.30 (6H, s), 2.32 (3H, s), 4.71 (1H), 7.09 (1H, d, J=2.1 Hz), 7.14 (2H, s), 7.36 (1H, d, J=2.1 Hz), 8.00 (1H).

EXAMPLE 24

2-(4-Hydroxy-3,5-dimethylphenyl)-5,6-dimethoxy-3-methylindole

Melting point: 196.3°–198.4° C.
IR, $\gamma_{max}^{KBr}$ (cm$^{-1}$): 3488, 1482, 1298, 1248, 1214, 1156.
NMR, $\delta_{(CD_3)_2SO}^{ppm}$: 2.23 (6H, s), 2.31 (3H, s), 3.76 (6H, s), 6.79 (1H, s), 6.90 (1H, s), 7.12 (2H, s), 8.22 (1H), 10.50 (1H).

EXAMPLE 25

2-(4-Hydroxy-3,5-dimethylphenyl)-4,5,6-trimethoxy-3-methylindole

Melting point: 177.5°–178.2° C.
NMR, $\delta_{CDCl_3}^{ppm}$: 2.28 (6H, s), 2.50 (3H, s), 3.80 (3H, s), 3.86 (3H, s), 3.99 (3H, s), 4.76 (1H, s), 6.52 (1H, s), 7.08 (2H, s), 7.80 (1H).

EXAMPLE 26

4,5-Ethylenedioxy-2-(4-hydroxy-3,5-dimethylphenyl)-3-methylindole

Melting point: 159.2°–161.2° C.
NMR, $\delta_{(CD_3)_2SO}^{ppm}$: 2.23 (6H, s), 2.46 (3H, s), 4.22 (4H, s), 6.47 (1H, d, J=8 Hz), 6.72 (1H, d, J=8 Hz), 7.10 (2H, s), 8.25 (1H).

EXAMPLE 27

2-(4-Hydroxy-3,5-dimethylphenyl)-5,6-methylenedioxy-3-methylindole

Melting point: 161.8°–162.1° C.
NMR, $\delta_{(CD_3)_2SO}^{ppm}$: 2.25 (6H, s), 2.28 (3H, s), 5.37 (2H, s), 6.80 (1H, s), 6.87 (1H, s), 7.13 (2H, s), 8.26 (1H).

EXAMPLE 28

2-(4-Hydroxy-3,5-dimethylphenyl)-5-methoxy-3-methyl-6-trifluoromethylindole

Melting point: 173.4°–174.3° C.
NMR, $\delta_{CDCl_3}^{ppm}$: 2.25 (6H, s), 2.32 (3H, s), 3.88 (3H, s), 4.73 (1H, s), 6.97 (1H, s), 7.07 (2H, s), 7.39 (1H, s), 7.82 (1H).

EXAMPLE 29

(a) 3.6 g of 4-hydroxy-3,5-dimethylpropiophenone, 3.5 g of 4-methoxyphenylhydrazine hydrochloride and 2.0 g of potassium acetate were added to 100 ml of ethanol, and the mixture was stirred at 40° to 50° C. for 30 minutes. After the reaction, the solvent was evaporated, and the residue was extracted with ether and washed with water. After the solvent was evaporated, the crystals obtained were recrystallized from methylene chloride-hexane to obtain 4-hydroxy-3,5-dimethylpropiophenone 4-methoxyphenylhydrazone.

Melting point: 126.1°–127.5° C.
IR, $\nu_{max}^{KBr}$ (cm$^{-1}$): 3396, 1516, 1486, 1220, 1192, 1132, 1104, 1032, 822.
NMR, $\delta_{(CD_3)_2SO}^{ppm}$: 1.05 (3H, t, J=8 Hz), 2.2 (6H, s), 2.69 (2H, q, J=8 Hz), 3.63 (3H, s), 6.74 (2H, d, J=8 Hz), 7.12 (2H, d, J=8 Hz), 7.27 (2H, s), 8.1 (1H).

(b) 11.9 g of the hydrazone obtained in (a) above was dissolved in 50 ml of isopropanol, and 9 g of a 18.6% isopropanol solution of hydrogen chloride was added. The mixture was refluxed for 20 hours. Water was added to the reaction mixture. The precipitated crystals were collected by filtration, dissolved in ethyl acetate, and washed with 2N-hydrochloric acid, water, a saturated aqueous solution of sodium bicarbonate, and water. The organic layer was dried, and the solvent was evaporated. The crude crystals were recrystallized from ethanol-hexane to obtain 2-(4-hydroxy-3,5-dimethylphenyl)-5-methoxy-3-methylindole.

EXAMPLE 30

(a) 13.6 g of 2,6-dimethylanisole was dissolved in 30 ml of methylene chloride, and 16 g of anhydrous aluminum chloride was added. Then, with water cooling, 11 g of propionyl chloride was added dropwise. The mixture was stirred at room temperature for 1 hour. The reaction mixture was poured into ice water, and the organic layer was separated and washed with water. The solvent was evaporated to give 18.7 g of 2,6-dimethyl-4-propionylanisole.

IR, $\nu_{max}^{film}$ (cm$^{-1}$): 1690.
NMR, $\delta_{CDCl_3}^{ppm}$: 1.19 (3H, t, J=7 Hz), 2.33 (6H, s), 2.93 (2H, q, J=7 Hz), 3.73 (3H, s), 7.62 (2H, s).

(b) 5.0 g of 2,6-dimethyl-4-propionylanisole and 2.8 g of phenylhydrazine were dissolved in 30 ml of ethanol. A small amount of acetic acid was added under reflux for 30 minutes. After cooling, 10 ml of a 20% ethanol solution of hydrogen chloride was added to the reaction mixture, and the mixture was refluxed for 1.5 hours. The reaction mixture was cooled, poured into water, extracted with benzene, washed with water, and dried. The solvent was evaporated, and the residue was crystallized from benzene-hexane to give 4.3 g of 2-(4-methoxy-3,5-dimethylphenyl)-3-methylindole.

Melting point: 108.0°–109.7° C.
IR, $\nu_{max}^{KBr}$ (cm$^{-1}$): 3285, 2930, 2890, 1440, 1235, 730.
NMR, $\delta_{CDCl_3}^{ppm}$: 2.32 (6H, s), 2.40 (3H, s), 3.73 (3H, s), 7.0–7.70 (6H, m), 7.9 (1H).

(c) 4.3 g of 2-(4-methoxy-3,5-dimethylphenyl)-3-methylindole and 13 g of pyridinium chloride were reacted at 200° C. for 1.5 hours. The reaction mixture was cooled, poured into water, extracted with ethyl acetate, washed with water, and dried. The solvent was evaporated, and the residue was recrystallized from benzene-hexane to give 2.6 g of 2-(4-hydroxy-3,5-dimethylphenyl)-3-methylindole.

Melting point: 143.1°-143.8° C.

IR, $\nu_{max}^{KBr}$ (cm$^{-1}$): 3470, 3390.

NMR, $\delta_{CDCl_3}^{ppm}$: 2.3 (6H, s), 2.42 (3H, s), 4.68 (1H), 7.0-7.7 (6H, m), 7.85 (1H, s).

EXAMPLE 31

1.32 g of 5-bromo-2-(4-hydroxy-3,5-dimethylphenyl)-3-methylindole and 0.54 g of copper cyanide were added to 10 ml of N-methylpyrrolidone, and the mixture was refluxed for 4 hours. To the reaction mixture was added ethyl acetate, and the mixture was washed with 20% aqueous ammonia solution and water, and dried. The solvent was evaporated, and the residue was purified by silica gel column chromatography. Recrystallization of the crude product from ether-petroleum ether gave 5-cyano-2-(4-hydroxy-3,5-dimethylphenyl)-3-methylindole.

Melting point: 184.8°-185.6° C.

NMR, $\delta_{CDCl_3}^{ppm}$: 2.32 (6H, s), 2.40 (3H, s), 4.87 (1H, s), 7.15 (2H, s), 7.14-7.34 (2H, m), 7.85 (1H, d, J=2.0 Hz), 8.27 (1H).

EXAMPLE 32

5.0 g of 2-(4-hydroxy-3,5-dimethylphenyl)-3-methylindole was added to 100 ml of concentrated sulfuric acid, and the mixture was stirred at 0° C. Then, a solution of 1.76 g of sodium nitrate in 50 ml of concentrated sulfuric acid was added dropwise, and the mixture was stirred for 15 minutes. The reaction mixture was poured into ice-water, and extracted with ether. The resulting crude product was purified by silica gel column chromatography. Recrystallization from ether-hexane gave 2-(4-hydroxy-3,5-dimethylphenyl)-3-methyl-5-nitroindole.

Melting point: 229.4°-230.6° C.

NMR, $\delta_{CDCl_3}^{ppm}$: 2.27 (6H, s), 2.42 (3H, s), 3.30 (1H), 7.24 (2H, s), 7.39 (1H, d, J=8.0 Hz), 7.94 (1H, d—d, J=8.0 Hz, 3.1 Hz), 8.40 (1H, d, J=3.1 Hz), 8.50 (1H).

EXAMPLE 33

(a) 2-(4-Methoxy-3,5-dimethylphenyl)-3-methylindole was nitrated in the same way as in Example 32 to obtain 2-(4-methoxy-3,5-dimethylphenyl)-3-methyl-5-nitroindole.

Melting point: 143.5°-145.2° C.

(b) The resulting 5-nitro compound was dissolved in acetic acid, and after adding 5% palladium-carbon, hydrogenated for 6 hours. The catalyst was removed from the reaction mixture by filtration, and the solvent was evaporated. The residue was dissolved in ethyl acetate, washed with a saturated aqueous solution of sodium bicarbonate and water, and dried. The solvent was evaporated, and n-hexane was added. The precipitated crystals were collected by filtration to obtain 5-amino-2-(4-methoxy-3,5-dimethylphenyl)-3-methylindole.

NMR, $\delta_{CDCl_3}^{ppm}$: 2.31 (3H, s), 2.32 (6H, s), 3.72 (3H, s), 6.56 (1H, d—d, J=3.0 Hz, 12 Hz), 6.80 (1H, d, J=3.0 Hz), 7.06 (1H, d, J=12 Hz), 7.12 (2H, s), 7.70 (1H).

(c) The resulting 5-amino-2-(4-methoxy-3,5-dimethylphenyl)-3-methylindole was treated in the same way as in step (c) of Example 30 to give 5-amino-2-(4-hydroxy-3,5-dimethylphenyl)-3-methylindole.

Melting point: 184.1°-184.9° C.

IR, $\nu_{max}^{KBr}$ (cm$^{-1}$): 3385, 3330, 2900, 1475, 1452, 1325, 1198, 925.

NMR, $\delta_{CDCl_3}^{ppm}$: 2.29 (6H, s), 2.33 (3H, s), 3.40 (3H), 5.59 (1H, d—d, J=9.0 Hz, 2.7 Hz), 6.82 (1H, d, J=2.7 Hz), 7.11 (1H, d, J=9.0 Hz), 7.14 (2H, s), 7.68 (1H).

EXAMPLE 34

2-(4-Hydroxy-3,5-dimethylphenyl)-5-methoxy-3-methylindole was treated in the same way as in step (c) of Example 30 to give 5-hydroxy-2-(4-hydroxy-3,5-dimethylphenyl)-3-methylindole.

Melting point: 174.1°-175.5° C.

NMR, $\delta_{(CD_3)_2SO}$: 2.24 (6H, s), 2.26 (3H, s), 6.3-7.05 (3H, m), 7.15 (2H, s), 8.2 (1H).

EXAMPLE 35

1.6 g of 60% sodium hydride was suspended in 50 ml of dimethylformamide, and under ice cooling, 5-hydroxy-2-(4-hydroxy-3,5-dimethylphenyl)-3-methylindole was added. After stirring for 30 minutes, 2.8 g of 2-diethylaminoethylbromide hydrobromide was added. The mixture was stirred for 2 hours. The reaction mixture was poured into cold water, and extracted with ethyl acetate. The extract was purified by silica gel column chromatography, and then subjected to thin-layer chromatography to give 5-(2-diethylaminoethoxy)-2-(4-hydroxy-3,5-dimethylphenyl)-3-methylindole.

NMR, $\delta_{CDCl_3}^{ppm}$: 1.08 (6H, t, J=7.8 Hz), 2.26 (9H, s), 2.75 (6H, m) 3.98 (2H, m), 6.06 (1H), 6.90 (5H, m), 7.90 (1H).

EXAMPLE 36

5-Hydroxy-2-(4-hydroxy-3,5-dimethylphenyl)-3-methylindole and benzyl bromide were treated in the same way as in Example 35 to obtain 5-benzyloxy-2-(4-hydroxy-3,5-dimethylphenyl)-3-methylindole.

Melting point: 162.0°-162.4° C.

NMR, $\delta_{CDCl_3}^{ppm}$: 2.34 (9H, s), 4.81 (2H, s), 6.67 (1H, q, J=8 Hz, 3 Hz), 6.90 (1H, d, J=3 Hz), 7.12 (1H, d, J=8 Hz), 7.17 (2H, s), 7.40 (5H, s), 7.75 (1H).

EXAMPLE 37

0.8 g of 5-hydroxy-2-(4-hydroxy-3,5-dimethylphenyl)-3-methylindole was dissolved in 4 ml of pyridine, and under ice cooling, 0.26 g of acetyl chloride was added. The mixture was stirred at 40° C. for 1 hour. The reaction mixture was poured into ice water and extracted with ethyl acetate. The extract was washed with water, 2N hydrochloric acid and water, and purified by silica gel column chromatography to give 5-acetyloxy-2-(4-hydroxy-3,5-dimethylphenyl)-5-methylindole.

Melting point: 161.4°-162.2° C.

NMR, $\delta_{CDCl_3}^{ppm}$: 2.21 (6H, s), 2.30 (6H, s), 4.87 (1H), 6.65-7.25 (3H, m), 7.05 (2H, s), 7.85 (1H).

EXAMPLE 38

(a) 1.85 g of 5-amino-2-(4-methoxy-3,5-dimethylphenyl)-3-methylindole was dissolved in 20 ml of pyridine, and 1.51 g of p-toluenesulfonyl chloride was added. The mixture was stirred at room temperature for 1 hour. Ethyl acetate was added to the reaction mixture, and the mixture was washed with 5% hydrochloric acid and water, and dried. The solvent was evaporated, and the residue was purified by silica gel column chromatography to give 2-(4-methoxy-3,5-dimethylphenyl)-3-methyl-5-p-toluenesulfonylaminoindole.

Melting point: 192.3°–193.5° C.

(b) 1.5 g of the tosylamino compound obtained above and 0.28 g of potassium hydroxide were dissolved in 30 ml of acetone, and 0.56 g of 2-diethylaminoethylchloride was added. The mixture was stirred at room temperature for 20 hours. Ethyl acetate was added to the reaction mixture, and the mixture was washed with 5% hydrochloric acid and water and then dried. The solvent was evaporated, and the residue was purified by silica gel column chromatography to give 5-[N-(2-diethylaminoethyl)-N-p-toluenesulfonylamino]-2-(4-methoxy-3,5-dimethylphenyl)-3-methylindone.

NMR, $\delta_{(CD_3)_2SO}^{ppm}$: 1.13 (6H, t, J=8.0 Hz), 2.30 (9H, s), 2.40 (3H, s), 2.70–4.05 (8H, m), 3.68 (3H, s), 6.55–7.48 (9H, m), 7.58 (1H).

(c) 0.70 g of the tosyl compound obtained in (b) above and 0.37 g of phenol were dissolved in 8 ml of an acetic acid solution of hydrogen bromide. The mixture was stirred at 70° C. for 3 hours in a sealed condition. The reaction mixture was poured into ice water, and extracted with ethyl acetate. The extract was washed with 1N sodium hydroxide, and water, and dried. The solvent was evaporated, and the residue was purified by silica gel column chromatography. The product was dissolved in ethanol, and a 28% ethanol solution of hydrogen chloride was added. The mixture was concentrated. Ether was added, and the precipitated crystals were collected by filtration to give 5-(2-diethylaminoethylamino)-2-(4-hydroxy-3,5-dimethylphenyl)-3-methylindole dihydrochloride.

Melting point: 197.4°–198.2° C.

NMR, $\delta_{(CD_3)_2SO}^{ppm}$: 1.28 (6H, t, J=8.0 Hz), 2.25 (6H, s), 2.38 (3H, s), 3.21 (4H, q, J=8.0 Hz), 3.50–3.82 (4H, m), 7.18–7.45 (7H, m), 7.75 (1H).

EXAMPLE 39

In the same way as in Example 38, the following compounds were obtained.

(a) 5-(N-benzyl-N-p-toluenesulfonylamino)-2-(4-methoxy-3,5-dimethylphenyl)-3-methylindole Melting point: 197.0°–198.5° C.

(b) 5-Benzylamino-2-(4-hydroxy-3,5-dimethylphenyl)-3-methylindole hydrochloride.

Melting point: 204.4°–206.2° C.

NMR, $\delta_{(CD_3)_2SO}^{ppm}$: 2.24 (6H, s), 2.32 (3H, s), 4.50 (2H, s), 7.13–7.60 (10H, m).

EXAMPLE 40

The following compounds were obtained in the same way as in Example 38.

(a) 2-(4-Methoxy-3,5-dimethylphenyl)-3-methyl-5-(N-methyl-N-p-toluenesulfonylamino)indole Melting point: 184.1°–185.2° C.

(b) 2-(4-Hydroxy-3,5-dimethylphenyl)-3-methyl-5-methylaminoindole hydrochloride.

NMR, $\delta_{(CD_3)_2SO}^{ppm}$: 2.25 (6H, s), 2.37 (3H, s), 2.97 (3H, s), 7.21 (2H, s), 7.10–7.65 (5H, m), 11.27 (3H, m).

EXAMPLE 41

6.26 g of 4-hydroxy-3,5-dimethylpropiophenone 2-nitrophenylhydrazone and 60.6 g of zinc chloride were added to acetic acid, and the mixture was refluxed for 2 hours in a nitrogen stream. Ethyl acetate was added to the reaction mixture, and the mixture was washed with 1N aqueous sodium hydroxide solution and water, and dried. The solvent was evaporated, and the residue was purified by silica gel column chromatography. The resulting product was recrystallized from ether-benzene to give 2-(4-hydroxy-3,5-dimethylphenyl)-3-methyl-7-nitroindole.

Melting point: 178.4°–178.9° C.

NMR, $\delta_{(CD_3)_2SO}^{ppm}$: 2.28 (6H, s), 2.38 (3H, s), 3.28 (1H, s), 7.14 (1H, t, J=10 Hz), 7.23 (2H, s), 7.91 (1H, d–d, J=10 Hz, 2.0 Hz), 7.99 (1H, d–d, J=10 Hz, 2.0 Hz), 8.42 (1H, s).

EXAMPLE 42

2-(4-Hydroxy-3,5-dimethylphenyl)-3-methyl-7-nitroindole was treated in the same way as in step (b) of Example 33 to give 7-amino-2-(4-hydroxy-3,5-dimethylphenyl)-3-methylindole hydrochloride.

NMR, $\delta_{(CD_3)_2SO}^{ppm}$: 2.26 (6H, s), 2.39 (3H, s), 7.29 (2H, s), 6.95–7.60 (6H, m).

EXAMPLE 43

3 g of 4-n-propoxyaniline and 2.56 g of 4-(2-bromo-1-oxopropyl)-2,6-dimethylphenol were heated at 150° C. for 40 minutes in a stream of nitrogen. Ice water was added to the reaction mixture, and the mixture was extracted with ethyl acetate. The extract was purified by silica gel column chromatography, and recrystallized from ether-hexane to give 2-(4-hydroxy-3,5-dimethylphenyl)-3-methyl-5-n-propoxyindole.

Melting point: 124.2°–124.4° C.

NMR, $\delta_{CDCl_3}^{ppm}$: 1.05 (3H, t, J=7 Hz), 1.85 (2H, sextet, J=7 Hz), 2.30 (6H, s), 2.37 (3H, s), 3.97 (2H, t, J=7 Hz), 6.78 (1H, q, J=9 Hz, J=3 Hz), 6.98 (1H, d, J=3 Hz), 7.12 (2H, s), 7.16 (1H, d, J=9 Hz), 7.7 (1H).

EXAMPLE 44

(a) 2,6-Dimethylanisole and n-butyryl chloride were treated in the same way as in step (a) of Example 30 to give 4-n-butyryl-2,6-dimethylanisole.

NMR, $\delta_{CDCl_3}^{ppm}$: 1.0 (3H, t, J=7 Hz), 1.75 (2H, sextet, J=7Hz), 2.32 (6H, s), 2.90 (3H, s), 5.30 (1H, s), 7.65 (2H, s).

(b) The anisole obtained above and phenylhydrazine were treated in the same way as in step (b) of Example 30 to give 3-ethyl-2-(4-methoxy-3,5-dimethylphenyl)indole.

Melting point: 126.3°–127.4° C.

(c) The indole obtained above was treated in the same way as in step (c) of Example 30 to give 3-ethyl-2-(4-hydroxy-3,5-dimethylphenyl)indole.

Melting point: 106.8°–107.2° C.

NMR, $\delta_{CDCl_3}^{ppm}$: 1.32 (3H, t, J=8 Hz), 2.29 (6H, s), 2.88 (2H, q, J=8 Hz), 4.68 (1H), 7.0–7.7 (6H, m), 7.82 (1H).

EXAMPLE 45

4-n-Butyryl-2,6-dimethylphenol and 4-methoxyphenylhydrazine hydrochloride were treated in the same way as in Example 1 to give 3-ethyl-2-(4-hydroxy-3,5-dimethylphenyl)-5-methoxyindole.

Melting point: 176.4°–177.5° C. (recrystallized from acetone-hexane).

IR, $\nu_{max}^{KBr}$ (cm$^{-1}$): 3356, 1482, 1454, 1386, 1206, 1172, 1078.

NMR, $\delta_{CDCl_3}^{ppm}$: 1.29 (3H, t, J=0.6 Hz), 2.28 (6H, s), 2.82 (2H, q, J=0.6 Hz), 3.84 (3H, s) 4.68 (1H, s), 6.6–7.3 (3H, m), 7.1 (2H, s), 7.7 (1H).

EXAMPLE 46

(a) 2,6-Diethylanisole and propionyl chloride were treated in the same way as in step (a) of Example 30 to give 2,6-diethyl-4-propionylanisole.

IR, $\nu_{max}^{NaCl}$ (cm$^{-1}$): 2900, 1680, 1595, 1455, 1280, 1150, 1005.

(b) The anisole obtained above and phenylhydrazine were treated in the same way as in step (b) of Example 30 to give 2-(3,5-diethyl-4-methoxyphenyl)-3-methylindole.

Melting point: 95.7°–96.1° C.

(c) The indole obtained above was treated in the same way as in step (c) of Example 30 to give 2-(3,5-diethyl-4-hydroxyphenyl)-3-methylindole.

Melting point: 112.2°–112.4° C.

NMR, $\delta_{CDCl_3}^{ppm}$: 1.29 (6H, t, J=7.7 Hz), 2.44 (3H, s), 2.7 (4H, q, J=7.7 Hz), 4.73 (1H, s), 7.0–8.1 (7H, m).

EXAMPLE 47

The following compounds were obtained in the same way as in Example 46.

(a) 5-Chloro-2-(3,5-diethyl-4-methoxyphenyl)-3-methylindole

NMR, $\delta_{CDCl_3}^{ppm}$: 1.28 (6H, t, J=8 Hz), 2.37 (3H, s), 2.72 (4H, q, J=8 Hz), 3.76 (3H, s), 7.08–7.48 (5H, m), 7.91 (1H).

(b) 5-Chloro-2-(3,5-diethyl-4-hydroxyphenyl)-3-methylindole

Melting point: 137.5°–138.8° C.

NMR, $\delta_{CDCl_3}^{ppm}$: 1.28 (6H, t, J=8 Hz), 2.35 (3H, s), 2.65 (4H, q, J=8 Hz), 4.73 (1H, s), 7.07–7.48 (5H, m), 7.86 (1H).

EXAMPLE 48

2,6-Diethyl-4-propionylphenol and 4-methoxyphenylhydrazine hydrochloride were treated in the same way as in Example 1 to give 2-(3,5-diethyl-4-hydroxyphenyl)-5-methoxy-3-methylindole.

Melting point: 121.6°–124.0° C.

NMR, $\delta_{CDCl_3}^{ppm}$: 1.27 (6H, t, J=8 Hz), 2.38 (3H, s), 2.65 (4H, q, J=8 Hz), 3.84 (3H, s), 4.79 (1H, s), 6.68–7.72 (5H, m), 7.80 (1H).

EXAMPLE 49

In the same way as in Example 46, the following compounds were obtained.

(a) 2-(3,5-Diethyl-4-methoxyphenyl)-5-methoxy-3-methylindole

Melting point: 131.4°–132.2° C.

(b) 2-(3,5-Diethyl-4-hydroxyphenyl)-5-hydroxy-3-methylindole

Melting point: 181.4°–182.8° C.

NMR, $\delta_{CDCl_3}^{ppm}$: 1.3 (6H, t, J=7 Hz), 2.37 (3H, s), 2.70 (4H, q, J=7 Hz), 4.52 (1H, s), 4.76 (1H, s), 6.6–7.4 (3H, m), 7.19 (2H, s), 7.8 (1H, s).

EXAMPLE 50

4-n-Butyryl-2,6-diethylphenol and phenylhydrazine hydrochloride were treated in the same way as in Example 1 to give 3-ethyl-2-(3,5-diethyl-4-hydroxyphenyl)indole.

Melting point: 96.3°–96.7° C.

NMR, $\delta_{CDCl_3}^{ppm}$: 1.27 (6H, t, J=8.0 Hz), 1.31 (3H, t, J=8.0 Hz), 2.73 (4H, q, J=8.0 Hz), 2.86 (2H, q, J=8.0 Hz), 4.68 (1H, s), 6.97–7.64 (6H, m), 7.78 (1H).

EXAMPLE 51

(a) 2,6-Dimethylanisole and n-hexanoyl chloride were treated in the same way as in step (a) of Example 30 to give 4-n-hexanoyl-2,6-dimethylanisole.

NMR, $\delta_{CDCl_3}^{ppm}$: 0.7–2.0 (7H, m), 2.32 (6H, s), 2.91 (2H, t, J=7 Hz), 3.76 (3H, s), 7.65 (2H, s).

(b) The anisole obtained in (a) above and phenylhydrazine were treated in the same way as in step (b) of Example 30 to give 3-n-butyl-2-(4-methoxy-3,5-dimethylphenyl)indole.

Melting point: 76.8°–77.7° C.

(c) The indole obtained in (b) above was treated in the same way as in step (c) of Example 30 to give 3-n-butyl-2-(4-hydroxy-3,5-dimethylphenyl)indole.

Melting point: 83.1°–84.2° C.

NMR, $\delta_{CDCl_3}^{ppm}$: 0.7–2.0 (7H, m), 2.3 (6H, s), 2.87 (2H, t, J=8 Hz), 4.68 (1H), 7.0–7.7 (6H, m), 7.82 (1H).

EXAMPLE 52

(a) 2,6-Di-n-propylanisole and propionyl chloride were treated in the same way as in step (a) of Example 30 to give 4-propionyl-2,6-di-n-propylanisole.

NMR, $\delta_{CDCl_3}^{ppm}$: 0.97 (6H, t, J=5 Hz), 1.2 (3H, t, J=5 Hz), 1.65 (4H, m), 2.65 (4H, m), 2.94 (2H, q, J=5 Hz), 3.73 (3H, s), 7.61 (2H, s).

(b) The anisole obtained in (a) above and phenylhydrazine were treated in the same way as in step (b) of Example 30 to give 2-(4-methoxy-3,5-di-n-propylphenyl)-3-methylindole.

NMR, $\delta_{CDCl_3}^{ppm}$: 1.02 (6H, t, J=5 Hz), 1.7 (4H, m), 2.43 (3H, s), 2.66 (4H, m), 3.76 (3H, s), 7.20 (2H, s), 7.35 (4H, m), 7.90 (1H).

(c) The indole obtained in (b) was treated in the same way as in step (c) of Example 30 to give 2-(4-hydroxy-3,5-di-n-propylphenyl)-3-methylindole.

Melting point: 101.7°–101.9° C.

NMR, $\delta_{CDCl_3}^{ppm}$: 1.01 (6H, t, J=5 Hz), 1.70 (4H, m), 2.40 (3H, s), 2.60 (4H, m), 4.69 (1H, s), 7.14 (2H, s), 7.3 (4H, m), 7.85 (1H).

EXAMPLE 53

(a) 4-Hydroxy-3,5-dimethylpropiophenone and phenylhydrazine hydrochloride were treated in the same way as in step (a) of Example 29 to give 4-hydroxy-3,5-dimethylpropiophenone phenylhydrazone.

Melting point: 154.6°–154.8° C.

NMR, $\delta_{CDCl_3}^{ppm}$: 1.18 (3H, t, J=8.0 Hz), 2.25 (6H, s), 2.73 (2H, q, J=8.0 Hz), 4.65 (1H), 6.65–7.3 (6H, m), 7.35 (2H, s).

(b) The hydrazone obtained in (a) was treated in the same way as in step (b) of Example 29 to obtain 2-(4-hydroxy-3,5-dimethylphenyl)-3-methylindole.

EXAMPLE 54

(a) 4-Methoxy-3,5-dimethylpropiophenone and phenylhydrazine hydrochloride were treated in the same way as in step (a) of Example 29 to give 4-methoxy-3,5-dimethylpropiophenone phenylhydrazone as an oil.

NMR, $\delta_{CDCl_3}^{ppm}$: 1.18 (3H, t, J=8.0 Hz), 2.30 (6H, s), 2.62 (2H, q, J=8.0Hz), 3.68 (3H, s), 6.96 (5H, m), 7.38 (2H, s), 7.50 (1H).

(b) The hydrazone obtained in (a) above was treated in the same way as in step (b) of Example 29 to give 2-(4-methoxy-3,5-dimethylphenyl)-3-methylindole.

EXAMPLE 55

(a) 4-Hydroxy-3,5-dimethylpropiophenone and 3,4-dimethoxyphenylhydrazine hydrochloride were reacted in the same way as in step (a) of Example 29 to give 4-hydroxy-3,5-dimethylpropiophenone 3,4-dimethoxyphenylhydrazone.

Melting point: 133.8°–134.0° C.

NMR, $\delta_{CDCl_3}^{ppm}$: 1.19 (3H, t, J=8 Hz), 2.26 (6H, s), 2.66 (2H, q, J=8 Hz), 3.80 (3H), 3.87 (3H, s), 4.70 (1H), 6.7–7.0 (3H, m).

(b) The hydrazone obtained in (a) above was treated in the same way as in step (b) of Example 29 to give 2-(4-hydroxy-3,5-dimethylphenyl)-5,6-dimethoxy-3-methylindole.

EXAMPLE 56

(a) 4-Hydroxy-3,5-dimethylpropiophenone and 4-methylphenylhydrazine hydrochloride were treated in the same way as in step (a) of Example 29 to give 4-hydroxy-3,5-dimethylpropiophenone 4-methylphenylhydrazone.

Melting point: 136.5° C.

NMR, $\delta_{CDCl_3}^{ppm}$: 1.16 (3H, t, J=8.0 Hz), 2.25 (9H, s), 2.62 (2H, q, J=8.0 Hz), 4.55 (1H), 7.0 (4H, s), 7.2 (1H), 7.32 (2H, s).

(b) The hydrazone obtained in (a) above was treated in the same way as in step (b) of Example 29 to give 2-(4-hydroxy-3,5-dimethylphenyl)-3,5-dimethylindole.

EXAMPLE 57

(a) 4-Hydroxy-3,5-dimethylpropiophenone and 4-isopropoxyphenylhydrazone hydrochloride were treated in the same way as in step (a) of Example 29 to give 4-hydroxy-3,5-dimethylpropiophenone 4-isopropoxyphenylhydrazone as an oil.

NMR, $\delta_{CDCl_3}^{ppm}$: 1.2 (3H, t, J=8.0 Hz), 1.27 (6H, d, J=6.0 Hz), 2.23 (6H, s), 2.62 (2H, q, J=8.0 Hz9, 4.37 (1H, m, J=6.0 Hz), 4.76 (1H), 6.6–7.7 (4H, m), 7.31 (2H, s).

The following are examples of formulating drugs containing the compounds of formula (I) provided by this invention.

FORMULATION EXAMPLE A

|  | mg/capsule |
|---|---|
| Recipe 1-a for 50 mg capsules | |
| Active ingredient | 50 |
| Starch | 30 |
| Lactose | 27.8 |
| Magnesium stearate | 2.2 |
|  | 110 mg |
| Recipe 1-b for 100 mg capsules | |
| Active ingredient | 100 |
| Starch | 60 |
| Lactose | 55.6 |
| Magnesium stearate | 4.4 |
|  | 220 mg |

The active ingredient was well crushed, and mixed with starch, lactose and magnesium stearate. After thorough mixing, the mixture was filled in capsules.

FORMULATION EXAMPLE B

| Recipe for aerosols | % |
|---|---|
| Active ingredient | 1.5 |
| Sorbitan trioleate | 1.0 |
| Dichlorodifluoromethane | 58.5 |
| 1,2-Dichlorotetrafluoroethane | 39.0 |
|  | 100% |

Dichlorodifluoromethane was cooled to −55° C., and sorbitan trioleate was dispersed in it by a high-speed shear mixer. The active ingredient was then dispersed in the resulting dispersion, and 1,2-dichlorotetrafluoroethane was added. The mixture was filled in aerosol containers.

What is claimed is:

1. A compound represented by the formula

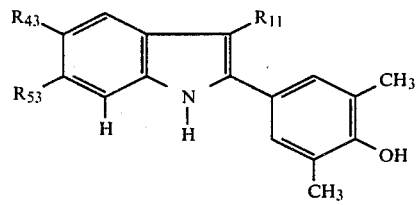

Wherein $R_{11}$ represents a methyl or ethyl group, $R_{43}$ represents a hydrogen atom, a methyl group, a methoxy group, an n-propoxy group, an isopropoxy group, an amino group, or a group of the formula

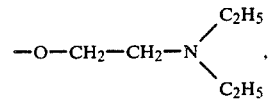

and $R_{53}$ represents a hydrogen atom or a methoxy group when $R_{43}$ is a methoxy group and represents a hydrogen atom when $R_{43}$ is other than a methoxy group, or a pharmaceutically acceptable salt thereof.

2. A pharmaceutical composition for inhibiting 5-lipoxygenase comprising a 5-lipoxygenase-inhibiting amount of a compound defined in claim 1 or its pharmaceutically acceptable salt in combination with a pharmaceutically acceptable carrier or diluent.

3. A method of treating a mammal suffering from a condition induced by a 5-lipoxygenase metabolite selected from the group consisting of asthma, an allergic disease and an ischemic myocardial infarction which comprises administering a 5-lipoxygenase inhibiting amount of compound defined in claim 1 or its pharamaceutically acceptable salt to the mammal.

4. The compound of claim 1, wherein $R_{11}$ is a methyl group.

5. The compound of claim 1, wherein the compound is a compound selected from the group consisting of 2-(4-hydroxy-3,5-dimethylphenyl)-5-methoxy-3-methylindole, 2-(4-hydroxy-3,5 dimethylphenyl)-3-methylindole, 2-(4-hydroxy-3,5,-dimethylphenyl)-3,5-dimethylindole, 5-amino-2-(4-hydroxy-3,5-dimethylphenyl)-3-methylindole, 2-(4-hydroxy-3,5-dimethylphenyl)-3-methyl-5-isopropoxyindole, or 2-(4-hydroxy-3,5-dimethylphenyl)-5,6-dimethoxy-3-methylindole.

* * * * *